(12) United States Patent
Guan et al.

(10) Patent No.: US 11,529,529 B2
(45) Date of Patent: Dec. 20, 2022

(54) MAGNETIC-VIBRATION AND MAGNETOELECTRIC THERAPY DEVICE

(71) Applicant: Zhengzhou Renhui Medical Equipment Co., Ltd., He'nan (CN)

(72) Inventors: Shichang Guan, He'nan (CN); Xiangqin Song, He'nan (CN)

(73) Assignee: Zhengzhou Renhui Medical Equipment Co., Ltd., Henan (CN)

( * ) Notice: Subject to any disclaimer, the term of this patent is extended or adjusted under 35 U.S.C. 154(b) by 583 days.

(21) Appl. No.: 16/677,649

(22) Filed: Nov. 7, 2019

(65) Prior Publication Data

US 2020/0282227 A1 Sep. 10, 2020

(30) Foreign Application Priority Data

Mar. 8, 2019 (CN) .......................... 201910175230.4

(51) Int. Cl.
*A61N 2/12* (2006.01)
*A61N 2/00* (2006.01)
*A61N 1/36* (2006.01)
*A61B 18/00* (2006.01)

(52) U.S. Cl.
CPC ............. *A61N 2/12* (2013.01); *A61N 1/3603* (2017.08); *A61N 1/36007* (2013.01); *A61N 2/002* (2013.01); *A61B 2018/00547* (2013.01)

(58) Field of Classification Search
CPC .. A61N 1/3603; A61N 1/36007; A61N 2/002; A61N 2/12; A61B 2018/00547; A61H 2201/10; A61H 2201/1207; A61H 2201/5007; A61H 2201/5043; A61H 23/0218
See application file for complete search history.

(56) References Cited

U.S. PATENT DOCUMENTS

2018/0229048 A1* 8/2018 Sikora .................... A61N 2/002

\* cited by examiner

*Primary Examiner* — Christine H Matthews
*Assistant Examiner* — Joshua Daryl D Lannu

(57) ABSTRACT

A magnetic-vibration and magnetoelectric therapy device, comprising an upper computer and a lower computer; the upper computer is used to send control instructions to the lower computer, and the lower computer is used to output stimulation signals acting on a human body based on the control instructions. The lower computer comprises a control unit, a magnetic vibration unit, a magnetoelectric unit and an electrical stimulation unit; the control unit is connected with the magnetic vibration unit, the magnetoelectric unit and the electrical stimulation unit respectively, the magnetic vibration unit is used to generate a vibrating magnetic field acting on a human body, the magnetoelectric unit is used to generate a vibrating rotating magnetic field acting on a human body, and the electrical stimulation unit is used to generate electrical stimulation signals acting on a human body. The device can be used to treat chronic prostatitis.

14 Claims, 8 Drawing Sheets

MAGNETIC-VIBRATION AND MAGNETOELECTRIC THERAPY DEVICE

CROSS-REFERENCE TO PRIOR APPLICATION

This application claims the benefit of Chinese Patent Application No. 201910175230.4 filed on Mar. 8, 2019, the contents of which are incorporated herein by reference.

TECHNICAL FIELD

The present invention relates to the technical field of medical devices, in particular to a magnetic-vibration and magnetoelectric therapy device.

BACKGROUND

When chronic inflammation occurs locally in a human body, traditional therapeutic methods such as medicines and surgical operations are not suitable for everyone; moreover, small dosages cannot achieve the therapeutic effect, and large dosages have great toxic side effects and may cause damage to other organs of a human body. The surgical operation is a traumatic therapeutic method with pain, post-operative infections and other risks. Therefore, a non-traumatic, painless and notably effective therapeutic method without toxic side effects is what the chronic inflammation of a human body needs most.

The magnetic-vibration and magnetoelectric therapy device applies to chronic prostatitis, induced symptoms and related diseases. The principle is to generate a resonance effect by combining a 180 mT oscillating magnetic field, magnetic vibration waves, mechanical waves and low frequency acoustic waves of the same frequency so that the therapeutic effects reach the lesion location, the human body generates a series of biological effects, the bioactivity of local tissue cells of the prostate and the permeability of biomembranes are enhanced, the local microcirculation of the prostate and the functions of the immune system are improved, thus promoting the absorption of inflammatory exudates to eliminate inflammation, relaxing the adhesion caused by inflammation to remove inflammatory infarction of glandular tubules, and finally achieving the clinical efficacy of eliminating perineal and pelvic pains, and improving urination, sperm vitality and quality of life; meanwhile, the treatment on acupoints with a 200 mT oscillating magnetic field, magnetic vibration waves and low frequency electric-impulse stimulation can adjust main and collateral channels, enhance the local immune function of the reproductive system and improve the therapeutic effect.

SUMMARY OF THE INVENTION

The technical problem to be solved by the present invention is to provide a magnetic-vibration and magnetoelectric therapy device for treating chronic prostatitis as well as related symptoms and diseases induced.

In order to solve the above technical problem, the technical solution of the present invention is as follows:

A magnetic-vibration and magnetoelectric therapy device comprises an upper computer and a lower computer; the upper computer is used to send control instructions to the lower computer, and the lower computer is used to output stimulation signals acting on a human body based on the control instructions;

The lower computer comprises a control unit, a magnetic vibration unit, a magnetoelectric unit and an electrical stimulation unit; the control unit is connected with the magnetic vibration unit, the magnetoelectric unit and the electrical stimulation unit respectively, the magnetic vibration unit is used to generate a vibrating magnetic field acting on a human body, the magnetoelectric unit is used to generate a vibrating rotating magnetic field acting on a human body, and the electrical stimulation unit is used to generate electrical stimulation signals acting on a human body.

Optionally, the magnetic vibration unit comprises a magnetic vibration drive circuit and a magnetic vibrator; the magnetic vibration drive circuit is used to convert the AC drive power into a half sine wave signal to drive the magnetic vibrator to vibrate.

Optionally, the magnetic vibration drive circuit comprises a first relay switch; the normally open contact of the first relay switch is connected with the magnetic vibrator, the first relay coil is connected with the control unit, and the control unit is used to control the on-off of the first relay switch.

Optionally, the magnetoelectric unit comprises a magnetoelectric drive circuit and a motor; the magnetoelectric drive circuit is used to convert the AC drive power into a DC signal to drive the motor to generate a vibrating rotating magnetic field.

Optionally, the magnetoelectric drive circuit comprises a second relay switch; the normally open contact of the second relay switch is connected with the motor, the second relay coil is connected with the control unit, and the control unit is used to control the on-off of the second relay switch.

Optionally, the electrical stimulation unit comprises a step-up circuit and electrical stimulation electrodes; the electrical stimulation electrodes are connected with the control unit and the step-up circuit respectively, the step-up circuit is used to convert low voltage direct current into high voltage direct current to supply power for the electrical stimulation electrodes, and the control unit outputs PWM signals to control the electrical stimulation electrodes to generate electrical stimulation signals.

Optionally, the therapy device also comprises a power supply unit; the power supply unit is connected with the control unit and used to supply power for the control unit;

The power supply unit comprises a rectification filter circuit and a step-down circuit; the input terminal of the rectification filter circuit is connected with an industrial frequency transformer, the output terminal of the rectification filter circuit is connected with the input terminal of the step-down circuit, and the output terminal of the step-down circuit is connected with the control unit.

Optionally, the upper computer comprises a PC terminal, a display device and an input-output device; the PC terminal is connected with the control unit through a communication unit, and the display device and the input-output device are connected with the PC terminal respectively.

Optionally, the display device is used to display patient information and therapeutic method information, the input-output device is used to select the therapeutic method and send it to the PC terminal, and the control unit receives the therapeutic method instruction sent from the PC terminal to control the magnetic-vibration and magnetoelectric therapy device to perform therapeutic actions.

Optionally, the therapeutic methods comprise magnetic vibration therapy, magnetoelectric therapy and/or electrical stimulation therapy, and the therapeutic actions comprise vibration of the magnetic vibrator, generation of the vibrating rotating magnetic field by the motor and/or generation of electrical stimulation signals by the electrical stimulation electrodes.

The present invention has the following advantages:

The magnetic-vibration and magnetoelectric therapy device supplies DC-DC power by voltage transformation, rectification and filtering at the power frequency voltage of 220V. After voltage transformation, the AC voltage outputs a half sine wave electrical signal of 50 HZ, 4.5V by half-wave rectification to drive the magnetic vibrator to generate vibrational waves and a magnetic field acting on a human body; at the same time, the single chip microcomputer generates a square wave with the frequency of 2 HZ-16 HZ and duty cycle of 1:1 to control 50-120V electrical signals to generate electrical stimulation acting on the human body for treatment;

The magnetic-vibration and magnetoelectric therapy device mainly achieves the purpose of treating related diseases through three physical effects: magnetic field, vibration and electrical stimulation; after the 180 mT and 200 mT medium intensity magnetic fields generated by the therapy device act on a human body when combined with vibration, the physical effects enable the human body to generate a series of biological effects so that the bioactivity of local tissue cells of the prostate and the permeability of biomembranes are enhanced, the local microcirculation of the prostate and the functions of the immune system are improved, thus promoting the absorption of inflammatory exudates to eliminate inflammation, relaxing the adhesion caused by inflammation to remove inflammatory infarction of glandular tubules, and eliminating pelvic pains, urgent urination, frequent urination and other symptoms caused by prostatitis.

In the figure, 1—body, 2—display screen, 3—keyboard, 4—mouse, 5—groove, 6—platform, 7—magnetoelectric treatment head, 8—magnetic vibration treatment head.

DETAILED DESCRIPTION OF THE PREFERRED EMBODIMENTS

The preferred embodiments of the present invention will be further described below in combination with the drawings. It should be stated here that the description of these embodiments is intended to help understand the present invention, but does not constitute a limitation on the present invention. In addition, the technical characteristics involved in the embodiments of the present invention described below can be combined with each other as long as there is no conflict between them.

Figure 1:
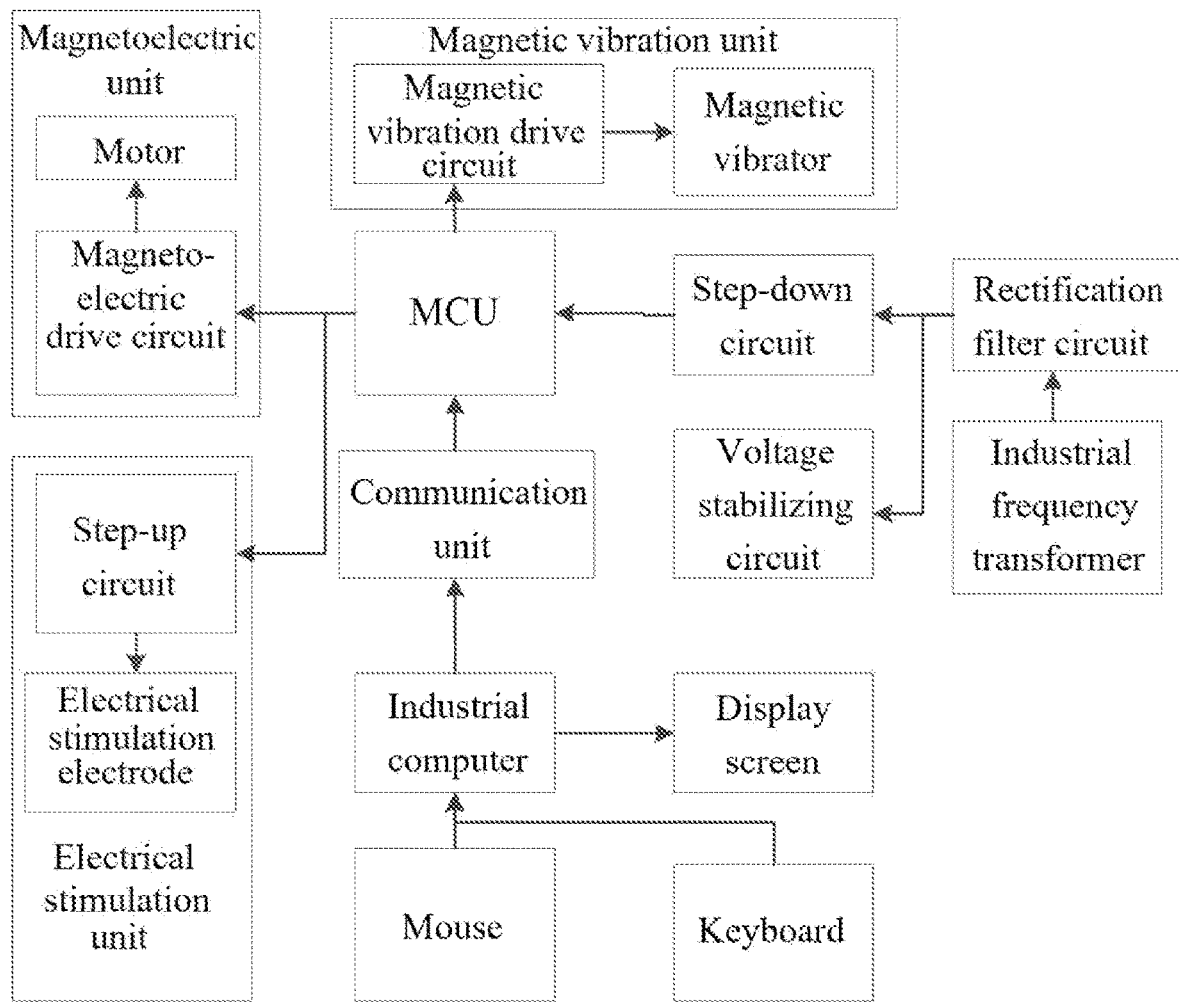
FIG. 1 is the structural block diagram of the magnetic-vibration and magnetoelectric therapy device of the present invention.

A magnetic-vibration and magnetoelectric therapy device, as shown in FIG. 1, comprises an upper computer and a lower computer; the upper computer and the lower computer are connected through a communication unit, the upper computer is used to send control instructions to the lower computer, and the lower computer is used to output stimulation signals acting on a human body based on the control instructions. In the embodiments of the present invention, the lower computer comprises a control unit, a magnetic vibration unit, a magnetoelectric unit and an electrical stimulation unit; the control unit is connected with the magnetic vibration unit, the magnetoelectric unit and the electrical stimulation unit respectively, the magnetic vibration unit is used to generate a vibrating magnetic field acting on a human body, the magnetoelectric unit is used to generate a vibrating rotating magnetic field acting on a human body, and the electrical stimulation unit is used to generate electrical stimulation signals acting on a human body.

Figure 2:
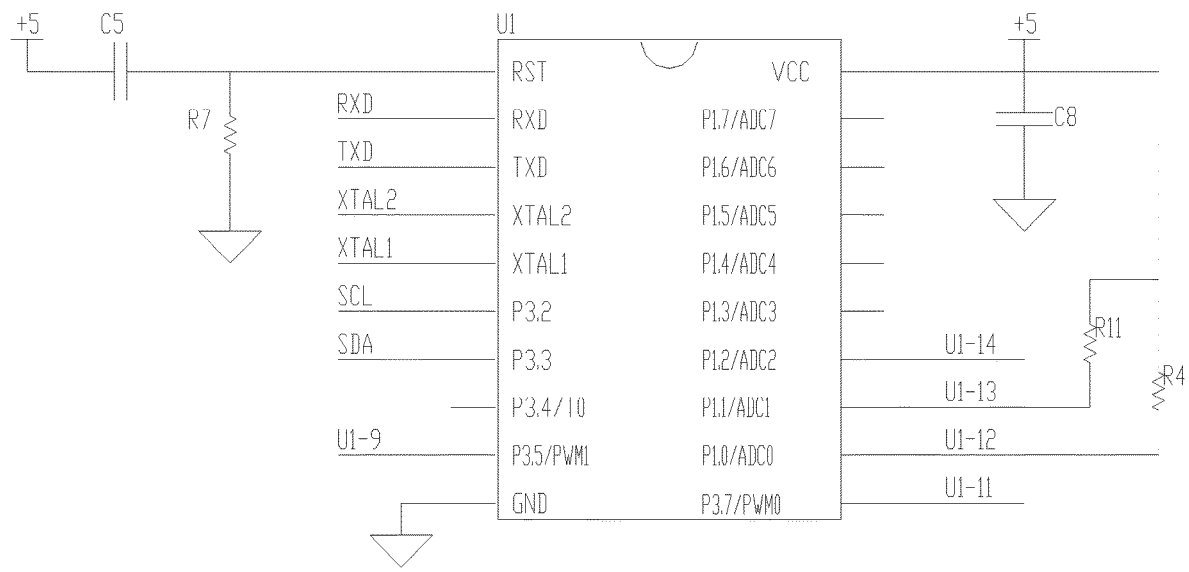
FIG. 2 is the circuit diagram of a MCU circuit in the magnetic-vibration and magnetoelectric therapy device of the present invention.

In the embodiments of the present invention, the control unit comprises an MCU circuit. FIG. 2 is the circuit diagram of the MCU circuit. As shown in FIG. 2, in the embodiments of the present invention, the MCU circuit comprises a single chip microcomputer STC12C5624 (hereinafter referred to as the single chip microcomputer U1). The reset pin (RST) of the single chip microcomputer U1 is connected with a reset circuit which comprises a divider resistor R7 and a protective capacitor C5, wherein one end of the protective capacitor C5 is connected with a +5V power supply, and the other end is connected to the reset pin (RST); one end of the divider resistor R7 is connected to the reset pin (RST), and the other end is grounded.

The power pin (VCC) of the single chip microcomputer U1 is connected with a +5V power supply and connected with a protective capacitor C8, and the other end of the protective capacitor is grounded.

Figure 3:
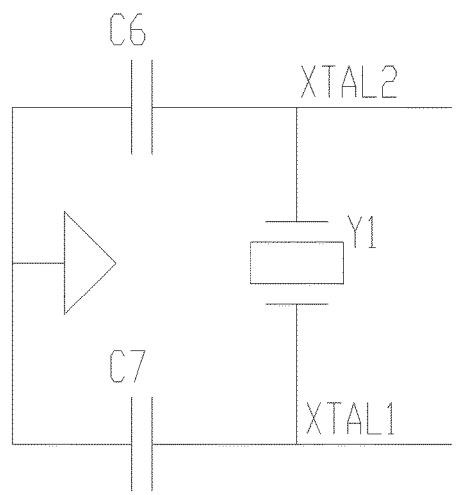
FIG. 3 is the circuit diagram of a clock oscillating circuit in the magnetic-vibration and magnetoelectric therapy device of the present invention.

A clock oscillating circuit is connected between two clock pins (XTAL1, XTAL2) of the single chip computer U1 and is used to provide a reference clock source for the single chip microcomputer U1. In the embodiments of the present invention, the clock oscillating circuit, as shown in FIG. 3, comprises a capacitor C6, a capacitor C7 and a crystal oscillator Y1. Two ends of the crystal oscillator Y1 are connected to two clock pins. One end of the capacitor C6 is grounded, and the other end is connected to the clock pin XTAL2. One end of the capacitor C7 is grounded, and the other end is connected to the clock pin XTAL1.

The magnetic vibration control pin (U1-13) of the single chip microcomputer U1 is connected with the magnetic vibration unit, the magnetoelectric control pin (U1-12) of the single chip microcomputer U1 is connected with the magnetoelectric unit, and the magnetic vibration control pin (U1-11) and the voltage control pin (U1-9) of the single chip microcomputer U1 are connected with the electrical stimulation unit.

In addition, the magnetic vibration control pin (U1-13) and the magnetoelectric control pin (U1-12) of the single chip microcomputer U1 are also connected with a +5V power supply respectively.

In the embodiments of the present invention, the +5V power supply of the control unit is powered by the power supply unit which comprises a rectification filter circuit and a step-down circuit. The input terminal of the rectification filter circuit is connected with the industrial frequency transformer, and the output terminal of the rectification filter circuit is connected with the input terminal of the step-down circuit. The output terminal of the step-down circuit is connected with the control unit. The industrial frequency transformer is used to reduce the voltage of the 220V, 50 Hz AC commercial power to 15V AC low voltage. The rectification filter circuit is used to rectify 15V AC low voltage to 20V DC power, and the step-down circuit is used to reduce the voltage of 20V DC power and output+5V stable DC power.

Figure 4:
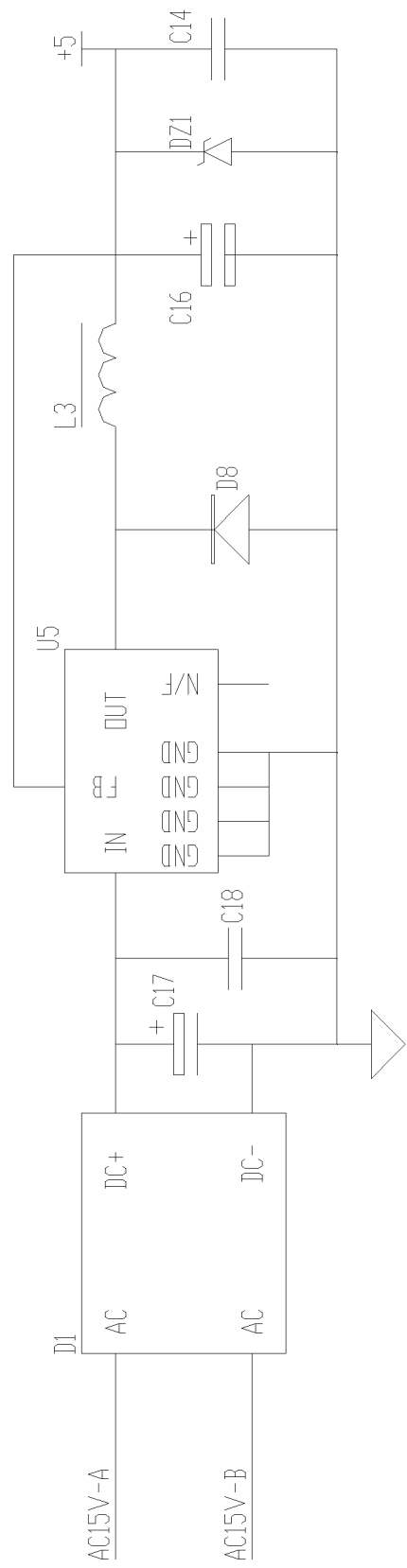
FIG. 4 is the circuit diagram of the power supply unit in the magnetic-vibration and magnetoelectric therapy device of the present invention.

FIG. 4 is the circuit diagram of the power supply unit, comprising a rectification filter circuit and a step-down circuit, as shown in the figure, the rectification filter circuit comprises a rectifier bridge D1, a filter capacitor C17 and a filter capacitor C18. The AC input terminal (AC pin) of the rectifier bridge D1 is connected with the commercial power. A filter capacitor C17 and a filter capacitor C18 are connected in series between the DC output terminals (DC+ pin, DC− pin) of the rectifier bridge D1 respectively. The DC− pin of the rectifier bridge D1 is also grounded.

The step-down circuit comprises a step-down chip U5 (model XL1509), a diode D8, an inductor L3, a capacitor C16, a voltage stabilizing diode DZ1 and a capacitor C14, wherein the input pin (IN) of the step-down chip U5 is connected with the output terminal of the rectification filter circuit, that is, the input pin (IN) of the step-down chip U5 is connected to the DC+ pin of the rectifier bridge D1. The diode D8 is connected between the output pin (OUT) of the step-down chip U5 and the ground terminal. A series circuit consisting of the inductor L3 and the capacitor C16 is also connected between the output pin (OUT) of the step-down chip U5 and the ground terminal. The node between the inductor L3 and the capacitor C16 is also connected to the feedback pin (FB) of the step-down chip U5. The voltage stabilizing diode DZ1 and the capacitor C14 are connected in series between the node between the inductor L3 and the capacitor C16 and the ground terminal respectively. The output pin (OUT) of the step-down chip U5 finally outputs+ 5V DC power.

Specifically, in the embodiments of the present invention, the magnetic vibration unit comprises a magnetic vibration drive circuit and a magnetic vibrator. The magnetic vibration drive circuit is used to convert the AC drive power into a half sine wave signal to drive the magnetic vibrator to vibrate, and the magnetic vibrator is installed in the magnetic vibration treatment head.

Figure 5:
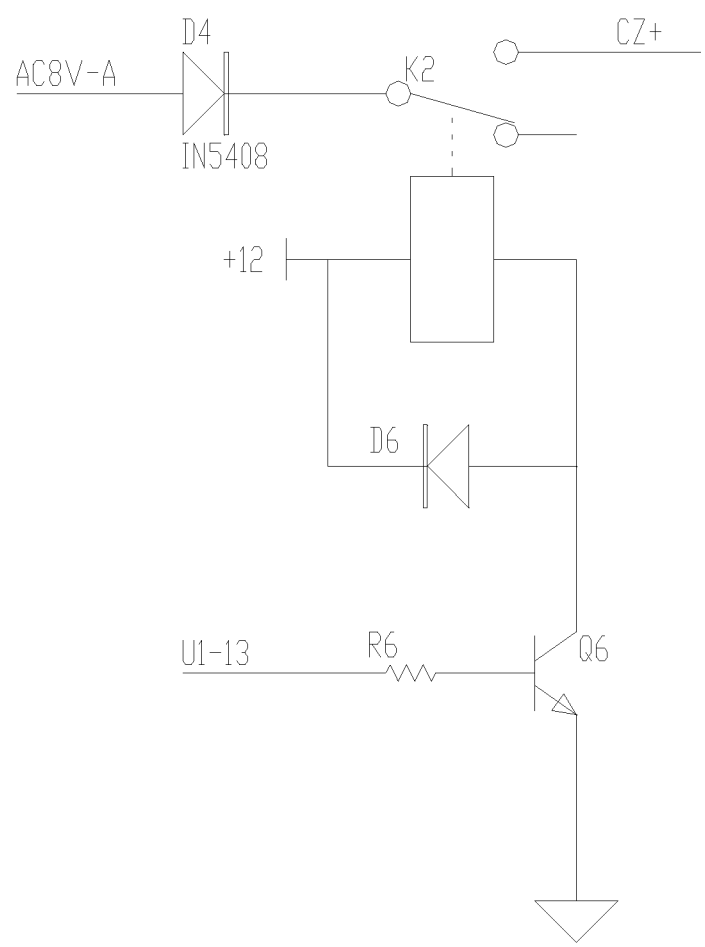
FIG. 5 is the circuit diagram of the magnetic vibration drive circuit in the magnetic-vibration and magnetoelectric therapy device of the present invention.

FIG. 5 is the circuit diagram of the magnetic vibration drive circuit, as shown in FIG. 5, which comprises a protective resistor R6, a triode driver Q6, a first relay switch, a rectifier diode D4 and a protection diode D6. In the embodiments of the present invention, the first relay switch is a time relay K2, the model of the time relay K2 is JDQ-5, the rectifier diode D4 is a NPN diode, and a rectifier diode D4 is connected in series between a movable contact of the time relay K2 and an AC8V AC power supply. The normally open contact of the time relay K2 is connected with the magnetic vibrator. One end of the coil of the time relay K2 is connected with a +12V power supply, and the other end is connected with the collector of the triode driver Q6. The emitter of the triode driver Q6 is grounded. A protective resistor R6 is connected in series between the base electrode of the triode driver Q6 and the magnetic vibration control pin (U1-13) of the single chip microcomputer U1. Both ends of the coil are also connected with the protection diode D6.

After the magnetic vibration control pin (U1-13) of the single chip computer U1 outputs a control signal, the triode driver Q6 controls the on or off of the time relay K2, and the AC8V AC power supply outputs a 4.5V, 50 Hz half sine wave signal by half-wave rectification through the rectifier diode D4. When the time relay K2 is on, the magnetic vibrator vibration can be driven to vibrate while acting on a human body.

In the embodiments of the present invention, the magnetoelectric unit comprises a magnetoelectric drive circuit and a motor. is used to convert the AC drive power into a DC signal to drive the motor to generate a vibrating rotating magnetic field. The motor is arranged in the magnetoelectric treatment head.

Figure 6:
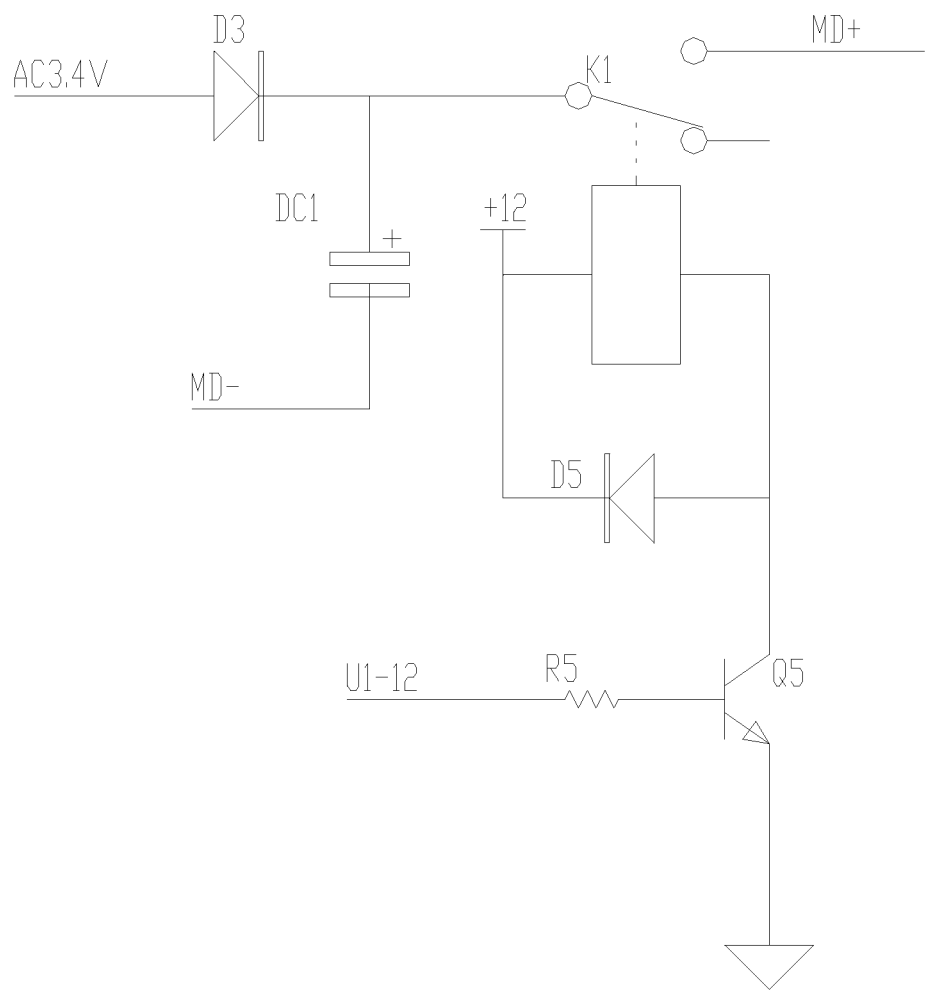
FIG. 6 is the circuit diagram of the magnetoelectric drive circuit in the magnetic-vibration and magnetoelectric therapy device.

FIG. 6 is the circuit diagram of the magnetoelectric drive circuit, as shown in FIG. 6, which comprises a protective resistor R5, a triode driver Q5, a second relay switch, a polar electrolytic capacitor DC1, a rectifier diode D3 and a diode D5. In the embodiments of the present invention, the second relay switch is a time relay K1, the model of the time relay K1 is JDQ-5, and the rectifier diode D4 is an NPN diode. A rectifier diode D3 is connected in series between a movable contact of the time relay K1 and an AC3.4V AC power supply. The electrolytic capacitor DC1 is connected in series between the node between the rectifier diode D3 and the movable contact of the time relay K1 and the motor negative electrode. The normally open contact of the time relay K1 is connected with the motor positive electrode. One end of the coil of the time relay K2 is connected with a +12V power supply, and the other end is connected with the collector of the triode driver Q5. The emitter of the triode driver Q5 is grounded. A protective resistor R5 is connected in series between the base electrode of the triode driver Q5 and the magnetoelectric control pin (U1-12) of the single chip microcomputer U1. Both ends of the coil are also connected with the protection diode D5.

After the magnetoelectric control pin (U1-12) of the single chip computer U1 outputs a control signal, the triode driver Q6 controls the on or off of the time relay K2, and the AC3.4V AC power supply outputs 1.5V DC power by half-wave rectification through the rectifier diode D4. When the time relay K1 is on, the motor can be driven to generate a vibrating rotating magnetic field acting on a human body.

In the embodiments of the present invention, the electrical stimulation unit comprises a step-up circuit and two electrical stimulation electrodes. The two electrical stimulation electrodes are connected with a control unit and a step-up circuit respectively. The step-up circuit is used to convert low voltage direct current into high voltage direct current to supply power to the electrical stimulation electrodes. The control unit outputs PWM signals to control the electrical stimulation electrodes to generate electrical stimulation signals. For ease of use, in the embodiments of the present invention, the electrical stimulation electrodes and the magnetic vibrator are put together on one magnetoelectric treatment head, that is, at least two magnetoelectric treatment heads are set on the magnetic-vibration and magnetoelectric therapy device, both of the magnetoelectric treatment heads contain motors, and the two electrical stimulation electrodes are arranged in two magnetoelectric treatment heads respectively.

Figure 7:
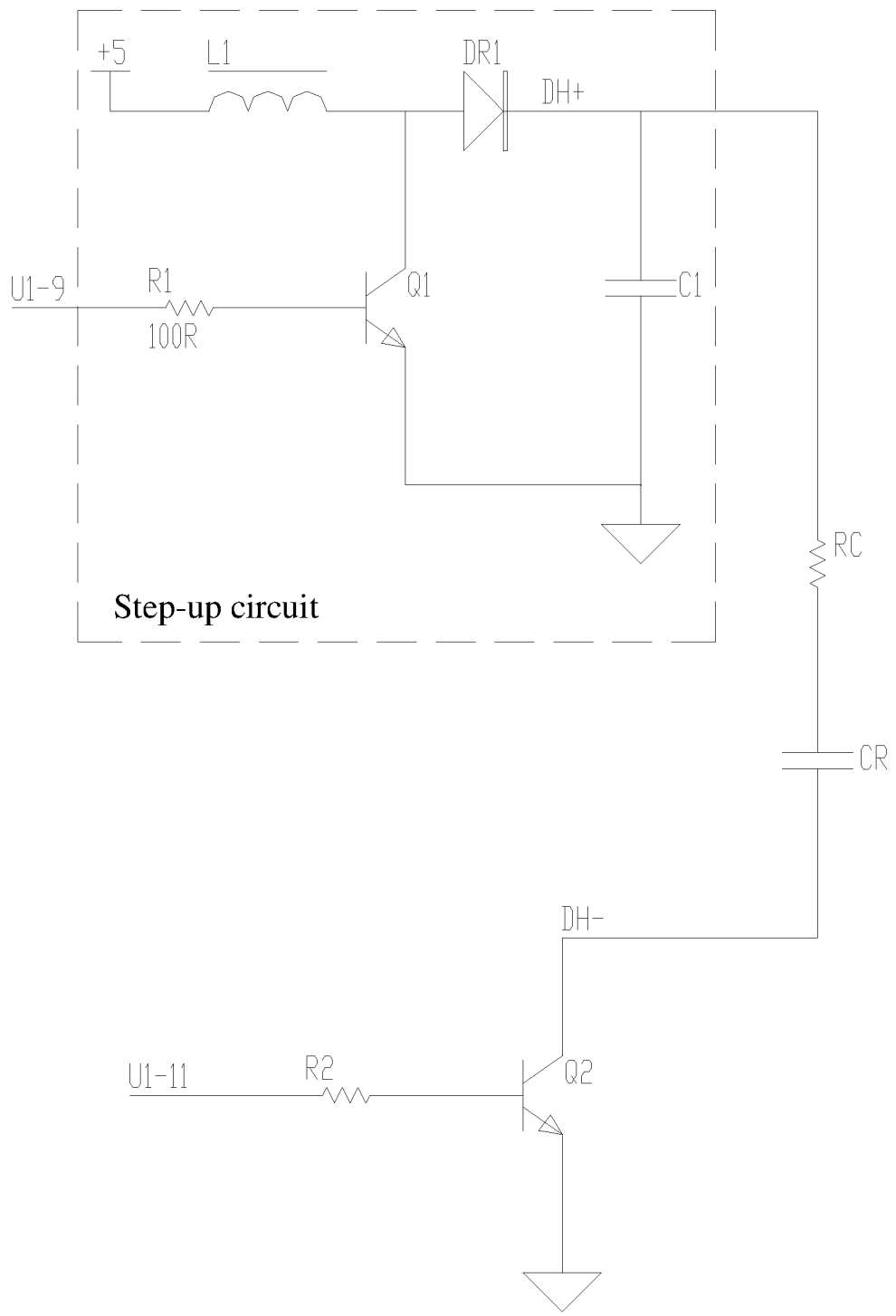
FIG. 7 is the circuit diagram of the electrical stimulation unit in the magnetic-vibration and magnetoelectric therapy device.

FIG. 7 is the circuit diagram of the electrical stimulation unit, as shown in FIG. 7, comprising a protective resistor R2, a triode Q2, a RC series circuit, a protective resistor R1, a triode Q1, a capacitor C1, a diode D1 and an inductor L1, wherein the protective resistor R1, the triode Q1, the capacitor C1, the diode D1 and the inductor L1 form the step-up circuit; one end of the protective resistor R2 is connected with the magnetic vibration control pin (U1-11) of the single chip computer U1, and the other end is connected with the base electrode of the triode Q2; the emitter of the triode Q2 is grounded; the collector of the triode Q2 is connected with the electrical stimulation electrodes (DH−) and the RC series circuit, respectively. The other end of the RC series circuit is connected with the electrical stimulation electrodes (DH+) and the step-up circuit respectively, wherein the RC series circuit comprises the resistor RC and the capacitor CR connected in series.

One end of the protective resistor R1 in the step-up circuit is connected with the voltage control pin (U1-9) of the single chip microcomputer U1, and the other end is connected with the base electrode of the triode Q1. The emitter of the triode Q1 is grounded, and a diode D1 is connected between the collector of the triode Q1 and the RC series circuit. The inductor L1 is also connected between the cathode of the diode D1 and the +5V power supply, and the capacitor C1 is connected between the cathode of the diode D1 and the ground terminal.

The voltage control pin (U1-9) of the single chip microcomputer U1 outputs a PWM signal to the step-up circuit so that it is boosted to 50-120V DC power; the magnetic vibration control pin (U1-11) of the single chip microcomputer U1 outputs 2-16 Hz pulse control signals at 1:1 (turn-on width: cut-off width), and the 50-120V DC power generated by the step-up circuit is converted into pulse electrical stimulation signals acting on a human body through the two electrical stimulation electrodes by controlling the on-off of the triode Q2.

Figure 8:
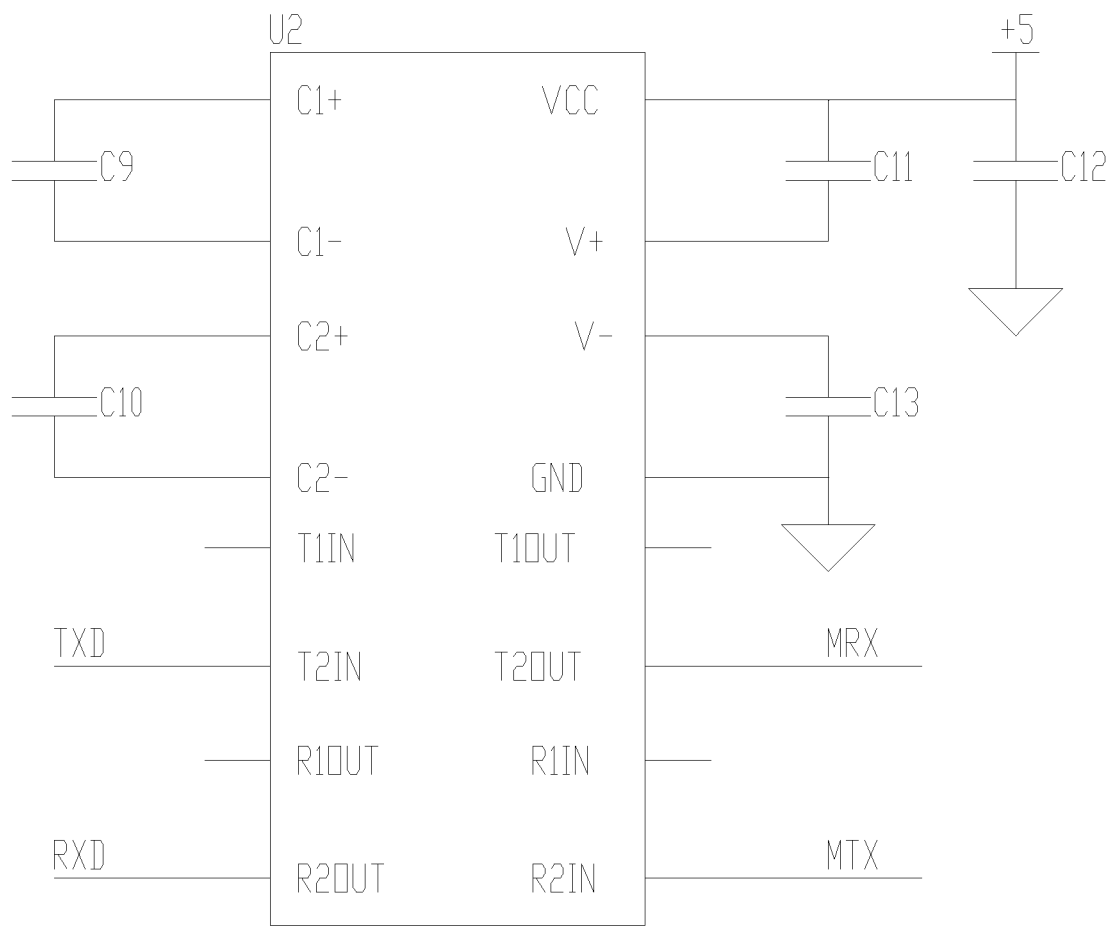
FIG. 8 is the circuit diagram of the communication unit in the magnetic-vibration and magnetoelectric therapy device.

The input pin (RXD) and output pin (TXD) of the single chip computer U1 are used to connect with the communication unit. FIG. 8 is the circuit diagram of the communication unit, as shown in FIG. 1, and the communication unit comprises a communication chip. In the embodiments of the present invention, the signal of the communication chip is MAX3232 (hereinafter referred to as U2), the input pin (RXD) of the single chip microcomputer U1 is connected with the receiver output pin (R2OUT) of U2, the output pin (TXD) of the single chip microcomputer U1 is connected with the receiver input pin (T2IN) of U2, and the transmitter output pin (R2OUT) of U2 and the transmitter input pin (T2IN) of U2 are used to connect and communicate with the upper computer. In addition, the power supply to the communication unit can also be supplied by the power supply unit, and a voltage stabilizing circuit shall also be set between the communication unit and the power supply unit.

Figure 9:
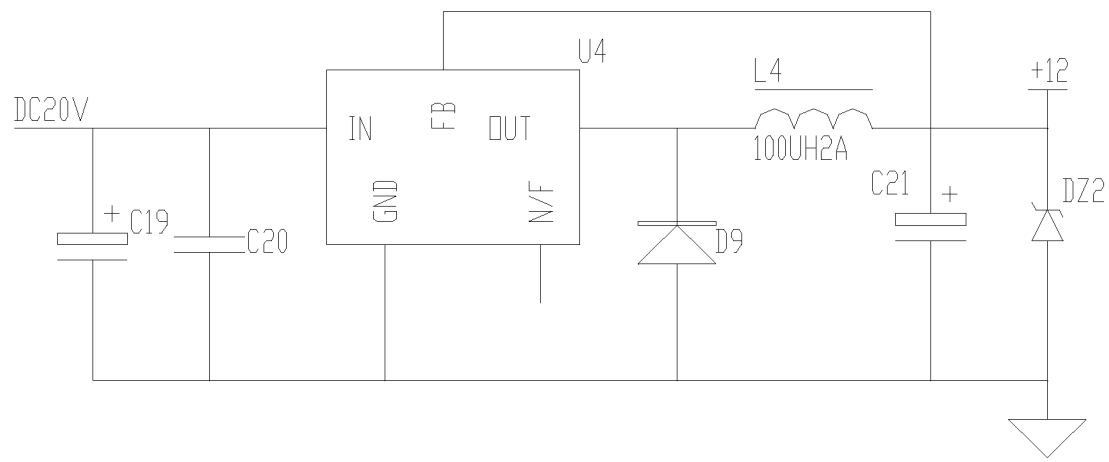
FIG. 9 is the circuit diagram of the voltage stabilizing circuit in the magnetic-vibration and magnetoelectric therapy device.

FIG. 9 is the circuit diagram of the voltage stabilizing circuit, as shown in FIG. 9, and the voltage stabilizing circuit comprises a voltage stabilizing chip. In the embodiments of the present invention, the voltage stabilizing chip has the model of LM2576 (hereinafter referred to as U4), the input pin (IN) of U4 is connected with 20V DC power, and a capacitor C19 and a capacitor C20 are also connected in series between the input pin (IN) of U4 and the ground terminal respectively. A diode D9 is inversely connected between the output pin (OUT) of U4 and the ground terminal. A series circuit consisting of an inductor L4 and a capacitor C21 is also connected between the output pin (OUT) of U4 and the ground terminal. The node between the inductor L4 and the capacitor C21 is also connected to the feedback pin (FB) of U4. A voltage stabilizing diode DZ2 and a capacitor C21 are connected in series between the node between the inductor L4 and the capacitor C21 and the ground terminal respectively. The output pin (OUT) of U4 finally outputs +12V DC power.

The upper computer comprises a PC terminal, a display device and an input-output device. The PC terminal is connected with the control unit through the communication unit. The display device and the input-output device are connected with the PC terminal respectively. In the embodiments of the present invention, the PC terminal comprises an industrial computer, the display device is a display screen 2, and the input-output device comprises a mouse 4 and a keyboard 3.

Figure 10:
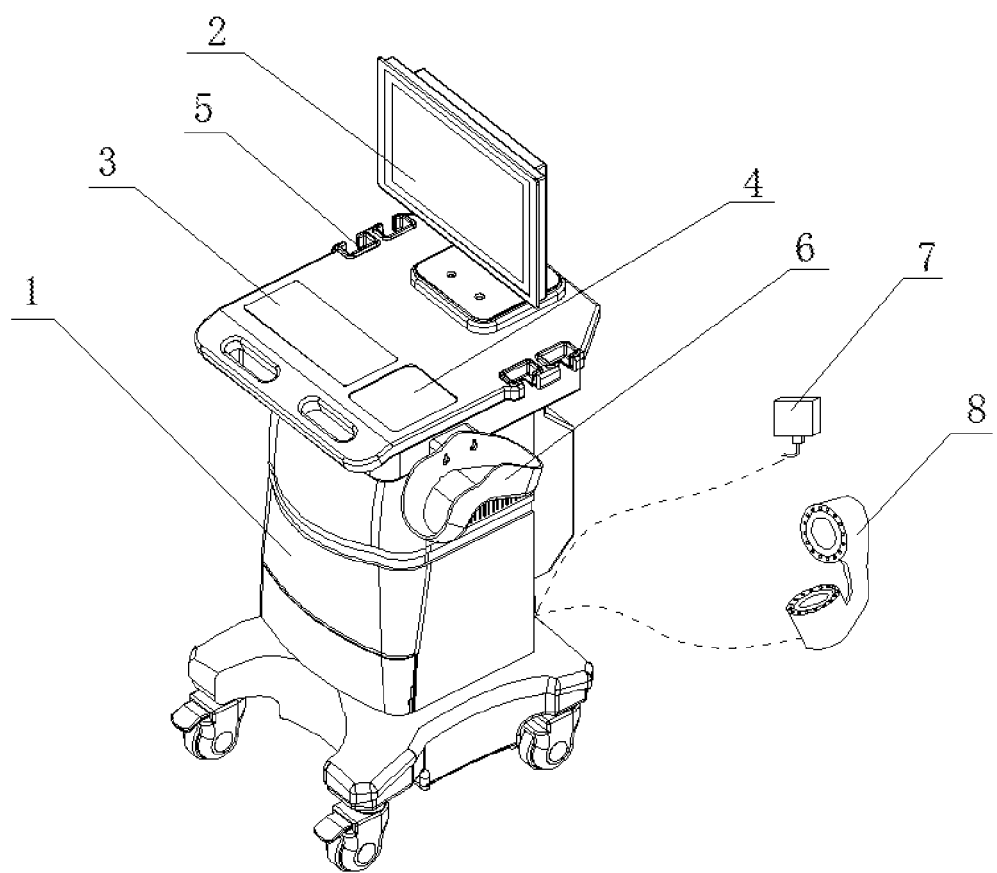
FIG. 10 is a structural schematic diagram of the magnetic-vibration and magnetoelectric therapy device.

FIG. 10 is a structural schematic diagram of the magnetic-vibration and magnetoelectric therapy device of the present invention, as shown in FIG. 10, wherein the display screen 2, the mouse 4 and the keyboard 3 are arranged on the therapy device body 1, and a plurality of grooves 5 are also formed on both sides of the body 1 for placing the magnetoelectric treatment head 7 in order to place the treatment heads. For example, in the embodiments of the present invention, four treatment heads are provided, and two grooves 5 are formed symmetrically on both sides of the body 1, respectively; in addition, a platform 6 for placing the magnetic vibration treatment heads 8 is also arranged on one side of the body 1. In order to facilitate the movement of the therapy device, universal wheels are also set at the bottom of the body 1.

In the embodiments of the present invention, the mouse 4 and the keyboard 3 are used to input patient information or select therapeutic methods and send them to the industrial computer. The display device is used to display patient information and therapeutic method information. The control unit receives therapeutic method instructions from the industrial computer to control the corresponding therapeutic actions of the magnetic vibration unit, the magnetoelectric unit and the electrical stimulation unit, wherein the therapeutic methods comprise magnetic vibration therapy, magnetoelectric therapy and/or electrical stimulation therapy, and the therapeutic actions comprise vibration of the magnetic vibrator, generation of the vibrating rotating magnetic field by the motor and/or generation of electrical stimulation signals by the electrical stimulation electrodes.

The use method of the magnetoelectric magnetic vibration therapy device of the present invention will be described in detail below:

The magnetic-vibration and magnetoelectric therapy device of the present invention is a physiotherapy apparatus which mainly achieves the purpose of treating related diseases through the three physical effects of magnetic field, vibration and electrical stimulation.

The 180 mT and 200 mT medium intensity magnetic fields can be combined with vibration while acting on a human body, that is, the magnetic vibration treatment heads 8 can act on the pubic symphysis or perineal position, and its physical effects can make the human body generate a series of biological effects: the bioactivity of local tissue cells of the prostate and the permeability of biomembranes are enhanced, the local microcirculation of the prostate and the functions of the immune system are improved, thus promoting the absorption of inflammatory exudates to eliminate inflammation, relaxing the adhesion caused by inflammation to remove inflammatory infarction of glandular tubules, and eliminating pelvic pains, frequent urination, urgent urination and other symptoms caused by prostatitis.

The magnetoelectric treatment head 7 acts on the position of Sanyinjiao acupoint (three inches above the prominence of the lateral malleolus of the foot) or Zusanli acupoint (three inches below the outside of the knee bone) to adjust the organ function of main and collateral channels. In clinical symptoms, diseases such as "strangury and turbid", "gonorrhea", "seminuria" and "white ooze" are mainly differentiated as the results of spleen-kidney deficiency, downward flow of damp and heat and phlegm and blood stasis due to long course of disease and difficult recovery. Zusanli is the key acupoint for invigorating the spleen, removing dampness and strengthening the body. It is often compatible with Sanyinjiao and other acupoints to treat disorder of genitourinary system. Sanyinjiao is a common and necessary key acupoint for disorder of genitourinary system. Either acupoint is one of the ten key acupoints of a human body. The two acupoints, when treated with the magnetoelectric treatment head 7 for physical therapy, are beneficial assistants to the direct action of the magnetic vibration treatment heads 8 on the prostate.

The embodiments of the present invention are described in detail above in combination with the attached drawings, but the present invention is not limited to the embodiments described. For those skilled in the art, various changes, modifications, substitutions and modifications of these embodiments still fall into the scope of protection of the present invention without departing from the principle and spirit of the present invention.

The invention claimed is:

1. A magnetic-vibration and magnetoelectric therapy device, comprising a control unit, a magnetic vibration unit, a magnetoelectric unit and an electrical stimulation unit, wherein:
   the control unit is connected with the magnetic vibration unit, the magnetoelectric unit and the electrical stimulation unit respectively;
   the control unit is an MCU (microcontroller unit);
   the magnetic vibration unit comprises a magnetic vibration drive circuit and a magnetic vibrator, wherein the magnetic vibration drive circuit converts an AC (alternating current) drive power into a half sine wave signal for driving the magnetic vibrator to vibrate, so as to generate a vibrating magnetic field;
   the magnetoelectric unit comprises a magnetoelectric drive circuit and a motor, wherein the magnetoelectric drive circuit converts the AC drive power into a DC (direct current) signal for driving the motor to generate a vibrating rotating magnetic field; and
   the electrical stimulation unit comprises a step-up circuit and two electrical stimulation electrodes, wherein:
     the electrical stimulation electrodes are connected with the MCU and the step-up circuit respectively;
     the step-up circuit converts low voltage direct current into high voltage direct current to supply power for the electrical stimulation electrodes; and
     the two electrical stimulation electrodes generate electrical stimulation signals under a control of PWM (pulse-width modulation) signals from the MCU.

2. The magnetic-vibration and magnetoelectric therapy device according to claim 1, wherein the magnetic vibration drive circuit comprises a first relay switch; a normally open contact of the first relay switch is connected with the magnetic vibrator, a first relay coil is connected with the MCU, and the MCU is used to control on-off of the first relay switch.

3. The magnetic-vibration and magnetoelectric therapy device according to claim 2, wherein the magnetoelectric drive circuit comprises a second relay switch; a normally open contact of the second relay switch is connected with the motor, a second relay coil is connected with the MCU, and the MCU is used to control on-off of the second relay switch.

4. The magnetic-vibration and magnetoelectric therapy device according to claim 3, further comprising a power supply unit, wherein:
   the power supply unit is connected with the MCU and used to supply power for the MCU; and
   the power supply unit comprises a rectification filter circuit and a step-down circuit, wherein an input terminal of the rectification filter circuit is connected with an industrial frequency transformer, an output terminal of the rectification filter circuit is connected with an input terminal of the step-down circuit, and an output terminal of the step-down circuit is connected with the MCU.

5. The magnetic-vibration and magnetoelectric therapy device according to claim 4, further comprising a PC terminal, a display device and an input-output device, wherein the PC terminal is connected with the MCU through a communication unit, and the display device and the input-output device are connected with the PC terminal respectively.

6. The magnetic-vibration and magnetoelectric therapy device according to claim 5, wherein the display device is used to display patient information and therapeutic method information, the input-output device is used to select a therapeutic method and send the therapeutic method to the PC terminal, and the MCU receives a therapeutic method instruction sent from the PC terminal to control the magnetic-vibration and magnetoelectric therapy device to perform a therapeutic action.

7. The magnetic-vibration and magnetoelectric therapy device according to claim 6, wherein the therapeutic method is magnetic vibration therapy, magnetoelectric therapy or electrical stimulation therapy, and the therapeutic action is vibration of the magnetic vibrator, generation of the vibrating rotating magnetic field by the motor, or generation of the electrical stimulation signals by the electrical stimulation electrodes.

8. The magnetic-vibration and magnetoelectric therapy device according to claim 1, further comprising a power supply unit, wherein:
   the power supply unit is connected with the MCU and used to supply power for the MCU; and
   the power supply unit comprises a rectification filter circuit and a step-down circuit, wherein an input terminal of the rectification filter circuit is connected with an industrial frequency transformer, an output terminal of the rectification filter circuit is connected with an input terminal of the step-down circuit, and an output terminal of the step-down circuit is connected with the MCU.

9. The magnetic-vibration and magnetoelectric therapy device according to claim 8, further comprising a PC terminal, a display device and an input-output device, wherein the PC terminal is connected with the MCU through a communication unit, and the display device and the input-output device are connected with the PC terminal respectively.

10. The magnetic-vibration and magnetoelectric therapy device according to claim 9, wherein the display device is used to display patient information and therapeutic method information, the input-output device is used to select a therapeutic method and send the therapeutic method to the PC terminal, and the MCU receives a therapeutic method instruction sent from the PC terminal to control the magnetic-vibration and magnetoelectric therapy device to perform a therapeutic action.

11. The magnetic-vibration and magnetoelectric therapy device according to claim 10, wherein the therapeutic method is magnetic vibration therapy, magnetoelectric therapy or electrical stimulation therapy, and the therapeutic action is vibration of the magnetic vibrator, generation of the vibrating rotating magnetic field by the motor, or generation of the electrical stimulation signals by the electrical stimulation electrodes.

12. The magnetic-vibration and magnetoelectric therapy device according to claim 1, further comprising a PC terminal, a display device and an input-output device, wherein the PC terminal is connected with the MCU through a communication unit, and the display device and the input-output device are connected with the PC terminal respectively.

13. The magnetic-vibration and magnetoelectric therapy device according to claim 12, wherein the display device is used to display patient information and therapeutic method information, the input-output device is used to select a therapeutic method and send the therapeutic method to the PC terminal, and the MCU receives a therapeutic method instruction sent from the PC terminal to control the magnetic-vibration and magnetoelectric therapy device to perform a therapeutic action.

14. The magnetic-vibration and magnetoelectric therapy device according to claim 13, wherein the therapeutic method is magnetic vibration therapy, magnetoelectric therapy or electrical stimulation therapy, and the therapeutic action is vibration of the magnetic vibrator, generation of the vibrating rotating magnetic field by the motor, or generation of the electrical stimulation signals by the electrical stimulation electrodes.

* * * * *